US009844662B2

(12) United States Patent
Leuthardt et al.

(10) Patent No.: US 9,844,662 B2
(45) Date of Patent: Dec. 19, 2017

(54) SYSTEM FOR STIMULATING BONE GROWTH, TISSUE HEALING AND/OR PAIN CONTROL, AND METHOD OF USE

(71) Applicant: Washington University, St. Louis, MO (US)

(72) Inventors: Eric C. Leuthardt, St. Louis, MO (US); Daniel W. Moran, St. Louis, MO (US); Matthew R. MacEwan, St. Louis, MO (US)

(73) Assignee: WASHINGTON UNIVERSITY, St. Louis, MO (US)

(*) Notice: Subject to any disclaimer, the term of this patent is extended or adjusted under 35 U.S.C. 154(b) by 719 days.

(21) Appl. No.: 14/212,648

(22) Filed: Mar. 14, 2014

(65) Prior Publication Data
US 2014/0200616 A1 Jul. 17, 2014

Related U.S. Application Data

(63) Continuation-in-part of application No. 12/089,104, filed as application No. PCT/US2006/038699 on Oct. 3, 2006, now Pat. No. 8,784,411.
(Continued)

(51) Int. Cl.
A61B 18/04 (2006.01)
A61N 1/05 (2006.01)
(Continued)

(52) U.S. Cl.
CPC ........... A61N 1/0558 (2013.01); A61N 1/205 (2013.01); A61B 17/7037 (2013.01);
(Continued)

(58) Field of Classification Search
CPC .................. A61N 1/0551; A61N 1/0558
See application file for complete search history.

(56) References Cited

U.S. PATENT DOCUMENTS 3,918,440 A * 11/1975 Kraus ............... A61B 17/6441
439/873
4,306,564 A * 12/1981 Kraus ................... A61B 17/58
607/51
(Continued)

FOREIGN PATENT DOCUMENTS

GB 2289416 A 11/1995
JP 2005021420 A 1/2005

OTHER PUBLICATIONS

International Search Report and Written Opinion of International Application No. PCT/US2015/020466, dated Jul. 2, 2015, 7 pages.
(Continued)

Primary Examiner — John R Downey
(74) Attorney, Agent, or Firm — Armstrong Teasdale LLP

(57) ABSTRACT

A system for use in stimulating bone growth, tissue healing, and/or pain control is described. The system includes a screw, a battery, a controller, and means for connecting the battery such that current is routed from the battery through the screw and thence to a target area of interest requiring treatment. The screw includes an elongate shaft having a length extending between opposite ends. The shaft has an insulating coating extending along at least a portion of the length. The thickness of the insulating coating at various portions of the shaft is modulated to optimally direct current to a target area of interest requiring treatment. The controller adjusts the duty cycle of the current flow over the treatment period.

6 Claims, 11 Drawing Sheets

Related U.S. Application Data

(60) Provisional application No. 60/813,633, filed on Oct. 3, 2005.

(51) Int. Cl.
  *A61N 1/20* (2006.01)
  *A61N 1/32* (2006.01)
  *A61N 1/36* (2006.01)
  *A61B 17/70* (2006.01)

(52) U.S. Cl.
  CPC ....... *A61B 17/7059* (2013.01); *A61B 17/7061* (2013.01); *A61N 1/326* (2013.01); *A61N 1/36071* (2013.01); *A61N 1/36103* (2013.01)

(56) References Cited

U.S. PATENT DOCUMENTS

| | | | |
|---|---|---|---|
| 4,318,792 A * | 3/1982 | Snow | C25D 15/02 204/510 |
| 4,333,469 A | 6/1982 | Jeffcoat et al. | |
| 4,548,208 A | 10/1985 | Niemi | |
| 4,549,546 A | 10/1985 | Kelly et al. | |
| 4,549,547 A | 10/1985 | Brighton et al. | |
| 4,590,946 A * | 5/1986 | Loeb | A61N 1/0558 600/375 |
| 4,854,865 A | 8/1989 | Beard et al. | |
| 4,889,111 A | 12/1989 | Ben-Dov | |
| 5,030,236 A | 7/1991 | Dean | |
| 5,196,015 A * | 3/1993 | Neubardt | A61B 17/8875 600/554 |
| 5,383,784 A * | 1/1995 | Sernetz | A61C 7/00 433/23 |
| 5,455,432 A * | 10/1995 | Hartsell | H01L 29/1054 257/347 |
| 5,531,787 A | 7/1996 | Lesinski et al. | |
| 5,683,386 A * | 11/1997 | Ellman | A61B 18/1402 606/41 |
| 5,743,844 A | 4/1998 | Tepper et al. | |
| 6,034,295 A | 3/2000 | Rehberg et al. | |
| 6,112,122 A | 8/2000 | Schwardt et al. | |
| 6,120,502 A * | 9/2000 | Michelson | A61B 17/1671 606/247 |
| 6,605,089 B1 | 8/2003 | Michelson | |
| 6,678,562 B1 | 1/2004 | Tepper et al. | |
| 6,778,861 B1 * | 8/2004 | Liebrecht | A61B 17/86 606/304 |
| 6,918,907 B2 * | 7/2005 | Kelly | A61B 18/1477 606/100 |
| 7,736,334 B2 * | 6/2010 | Mehier | A61B 18/04 604/113 |
| 2002/0016616 A1 | 2/2002 | McGraw et al. | |
| 2002/0133148 A1 * | 9/2002 | Daniel | A61B 18/1477 606/34 |
| 2004/0102828 A1 * | 5/2004 | Lowry | A61N 1/0531 607/116 |
| 2004/0181216 A1 | 9/2004 | Kelly et al. | |
| 2004/0243207 A1 * | 12/2004 | Olson | A61N 1/05 607/116 |
| 2005/0059972 A1 | 3/2005 | Biscup | |
| 2009/0054951 A1 * | 2/2009 | Leuthardt | A61N 1/205 607/46 |
| 2010/0106198 A1 * | 4/2010 | Adcox | A61B 17/8625 606/301 |
| 2010/0241229 A1 * | 9/2010 | Baehre | A61B 17/00491 623/16.11 |
| 2012/0059433 A1 | 3/2012 | Cowan et al. | |
| 2012/0185001 A1 * | 7/2012 | Nayet | A61B 17/8875 606/301 |

OTHER PUBLICATIONS

Extended European Search Report for Application No. 06816154.6, dated Nov. 4, 2009, 9 pages.

* cited by examiner

SYSTEM FOR STIMULATING BONE GROWTH, TISSUE HEALING AND/OR PAIN CONTROL, AND METHOD OF USE

CROSS-REFERENCE TO RELATED APPLICATIONS

This application is a continuation-in-part of U.S. patent application Ser. No. 12/089,104 filed Aug. 30, 2008, which claims priority from U.S. Provisional Patent Application Ser. No. 60/813,633 filed on Oct. 3, 2005 and PCT Patent Application No. PCT/US2006/038699 filed on Oct. 3, 2006, the contents of which are incorporated herein by reference in their entirety.

STATEMENT REGARDING FEDERALLY SPONSORED RESEARCH OR DEVELOPMENT

This invention was made with government support under Small Business Innovation Research Phase 1 Award No. 1248546 awarded by the National Science Foundation (NSF). The government has certain rights in the invention.

BACKGROUND

The present invention relates generally to a system for stimulating bone growth and tissue healing, and more particularly to a method and apparatus for stimulating bone growth and tissue healing by applying an electrical current to the bone and adjacent soft tissue through a partially insulated screw.

Bone growth is desirable in many instances, such as when vertebrae in a patient's spine are fused to overcome pain and other effects caused by inter-vertebral movement or intra-vertebral movement. Although bone growth occurs naturally, it can be stunted or stopped by various factors such as tobacco, alcohol and steroid usage, poor bone stock, and age. Moreover, stimulating bone growth to speed recovery is desirable in some instances, such as when an injured athlete wishes to return to her sport quickly. Other motivations for stimulating bone growth are to reduce chronic pain, to improve mobility, and avoid future complications. Thus, there is a need for stimulating bone growth in individuals.

Bone growth, tissue healing and pain control can be stimulated by various means. One such means for stimulating bone growth, tissue healing and pain control is by passing an electrical current through the bone. As one example, when fusing vertebrae in a patient's spine, various means have been used to stimulate bone growth. For example, some stimulators include wire electrodes embedded in bone fragments grafted to a region of the patient's back containing the vertebrae to be fused. Direct or alternating electrical current is applied to the electrodes to stimulate bone growth and fuse the fragments and adjoining vertebrae. To permit the current to be applied for extended periods of time while permitting the patient to be mobile, a generator is connected to the wire electrodes and implanted between the skin and muscle near the patient's vertebral column. The generator provides a continuous low amperage direct current (e.g., 20-100 µA) for an extended period of time (e.g., six or more months). After the vertebrae are fused, the generator and leads are surgically removed. Although these embedded electrodes are generally effective, the wire electrodes are susceptible to failure, requiring additional surgery to repair them. Moreover, placement of the wire electrodes is less than precise, allowing some of the current to pass through areas of tissue and bone where it is unneeded and where the current could potentially have adverse effects. Further, due to imprecise placement or lack of proximity to an area of interest, more energy must be provided to the electrodes than otherwise is necessary to be optimally effective. Thus, there are several drawbacks and potential problems associated with devices such as these.

Although small amounts of mechanical loading can stimulate growth, it is generally desirable to limit movement between the bones or bone fragments being fused. There are several known means for limiting bone movement. Among these means for limiting bone movement are plates, rods and screws. The plates and rods are typically held in position by screws which are mounted in the bone or bones being fused. FIG. 1 illustrates screws (generally designated by 10) driven into a vertebra 12 to immobilize the vertebra. As previously mentioned, the screws 10 are used for attaching rods 14 and/or plates (not shown) to vertebrae to hold the vertebrae in position while they fuse. Although these screws 10 work well for their intended purpose, they only provide mechanical fixation, and do not provide other potential benefits, such as facilitating electrical stimulation of the region and lack of adapting with changing tissue environments. In addition, with such conventional screws, undesirable complications may include loosening over time; being prone to pullout; being prone to infection; and not being useful in degraded osteoporotic or compromised bone. Moreover, if electrical stimulation were applied to bones using conventional screws, the screws 10 would not focus therapeutic stimulation and bone growth to anatomical areas where it is most desired and/or needed. Rather, they could potentially conduct current to areas of tissue and bone where the current is unneeded and where the current could potentially have adverse effects. Thus, there are drawbacks and potential problems associated with conventional screws such as these.

Beyond the well-defined role of electrical fields within bone formation, electrical fields have also shown significant promise in aiding healing and recovery in nerve and spinal cord injury. Stimulating tissue healing with electrical currents has been demonstrated to be efficacious in animal models and is now being attempted experimentally in human subjects. Further, spinal cord and nerve root injury has been known to cause associated debilitating pain syndromes which are resistant to treatment. These pain syndromes also have shown improvement with pulsed electrical stimulation. Given these findings, it is envisioned that a system and/or an apparatus providing a specified and confined electrical field through bony constructs and adjacent tissue (e.g., neural tissue) will facilitate an enhanced recovery from spinal cord and nerve injury, including improved functional outcome, better wound healing, and a higher level of pain control.

In U.S. Pat. No. 3,918,440, Kraus teaches the use of alternating current (A.C.) for assisting in the healing of bone damage. A.C. current carries several disadvantages. A.C. current relies on a complex power supply. In addition, it is more difficult to predict and control the spatial distribution of A.C. current within a body, since current may flow both through resistive and capacitive paths. Overall, substitution of D.C. for A.C. current results in system simplifications and opportunity to improve precision in targeting treatment to particular areas of interest within the body, while avoiding collateral damage to surrounding tissues. D.C. current is potentially advantageous in that required energy can be provided by batteries. However, it is critically important to properly size the battery powering a D.C. stimulation system to prevent premature interruption of the scheduled treatment. In fact, engineering tradeoffs include at least battery size, voltage, amp-hours, self-discharge rate, cost, and form factor. Clearly, there is a need for a D.C. stimulation system that optimally conserves power and allows for stimulation of bone growth and tissue healing. A smaller, lower cost battery will lead to increased patient mobility and comfort.

SUMMARY

In one aspect, a system for stimulating at least one of bone growth, tissue healing, and pain control is provided, wherein the system exerts both spatial and temporal control over D.C. current flow. The system comprises a D.C. battery and means for connecting the positive terminal of the battery to a screw that is inserted into a portion of a body requiring bone growth, tissue healing, or pain control, thereby directing current to a targeted area. In addition, the system comprises means to direct current exiting the body to the negative terminal of the battery, and controller means to controllably adjust the duty cycle of the current according to a prescribed schedule.

In one aspect, a screw for use in stimulating at least one of bone growth, tissue healing, and pain control is provided. The screw generally comprises an elongate shaft having a length extending between opposite ends, an exterior surface, and a screw thread formed on the exterior surface of the shaft and extending along at least a portion of the length of the shaft. The shaft also has an insulating coating extending along at least a portion of the length. The screw further comprises a head adjacent one end of the shaft for engaging the screw to rotate the screw and thereby drive it into bone, and an electrical conductor electrically connectable to the shaft for conveying current through the shaft. A thickness of the insulating coating at a first portion of the shaft is greater than a thickness of the insulating coating at a second portion of the shaft.

In another aspect, an apparatus for stimulating at least one of bone growth, tissue healing, and pain control is provided. The apparatus generally comprises an electrical power source and a plurality of electrodes. The plurality of electrodes are electrically connected to the electrical power source with at least one of the electrodes having a tip adapted for screwing into a patient and an insulating coating extending along at least a portion of its length. The insulating coating at a first portion of electrode is sufficiently thick to substantially prevent flow of current, while the insulating coating at a second portion of the electrode is sufficiently thin to substantially allow flow of current.

In yet another aspect, a method of stimulating at least one of bone growth, tissue healing and pain control is provided. The method generally comprises inserting a first and second electrode into a patient with the second electrode inserted at a predetermined distance from the first electrode, and applying an electric current to at least one of the first electrode and the second electrode. A thickness of an insulating coating at a second portion of the first electrode is greater than a thickness of the insulating coating at the first portion of the first electrode, and a thickness of an insulating coating at a second portion of the second electrode is greater than a thickness of the insulating coating at the first portion of the second electrode such that the electric current passes through the patient between the first portion of the first electrode and the first portion of the second electrode.

In another aspect, a method of producing an electrode is provided. The method generally comprises the formation of an electrode where the thickness of an insulating coating at a second portion of the electrode is greater than a thickness of the insulating coating at the first portion of the electrode. The method comprises the controlled immersion of a metallic electrode into a bath, application of an electrical charge or current, and controlled extraction of the metallic electrode from the bath. The depth of immersion, orientation of immersion, time of immersion, rate of immersion, composition of the bath, polarity of the electric charge, amplitude of the electric charge, rate of extraction, and distance of extraction may be controlled in order to achieve specific thicknesses of insulating coatings on the electrode surface.

In another embodiment, a portion of the length of the electrode may be uniformly coated such that the thickness of the insulating coating is the same over the entire length of the insulating coating. The relative length of the coated region of the electrode may therefore be varied from 50% to 95% of the length of the electrode. In this particular embodiment a method may be employed to achieve a uniform coating over a portion of the length of the electrode. The method generally comprises the rapid immersion of the metallic electrode into a bath along a predetermined orientation of immersion and up to a predetermined depth of immersion. The method further comprises a predetermined polarity of the electric charge, amplitude of the electric charge, and time of immersion. Finally, the method comprises the rapid and complete extraction of the metallic electrode from the bath.

In another embodiment, the coated portion of the electrode comprises 100% of the length of the electrode and the thickness of the coating is greatest at one end of the electrode and decreases along the entire length of the electrode. For example, in one embodiment the thickness of the coating is approximately 400 nanometers at the end of the electrode and decreases in thickness until it reaches approximately zero near the opposite end of the electrode. According to this embodiment, the insulating thickness can be graded, for example, linearly or exponentially. Again, the specific dimensions are merely illustrative and in other embodiments the thickness of the coating along the length of the electrode may vary from those depicted without departing from the scope of this disclosure. In this particular embodiment a method may be employed to achieve a graded coating over substantially the entire length of the electrode. The method generally comprises the rapid immersion of the metallic electrode into a bath along a predetermined orientation of immersion and up to a predetermined depth of immersion. The method further comprises a predetermined polarity of the electric charge, amplitude of the electric charge, and time of immersion. Finally, the method comprises the slow and controlled extraction of the metallic electrode from the bath along a pre-determined and variable-speed course of extraction. Specifically, extraction of the electrode from the bath at a constant rate will produce a linear gradient in the thickness of the coating from one end of the electrode to the other end of the electrode. Furthermore, extraction of the electrode from the bath at a progressively decreasing rate will produce an exponential gradient in the thickness of the coating from one end of the electrode to the other end of the electrode. As will be apparent to those skilled in the arts, any arbitrary gradient of insulating coating can be produced by appropriate adjustment of the rate of extraction of the electrode from the bath.

In another embodiment, the coated portion of the electrode comprises between 50% and 95% of the length of the electrode and the thickness of the coating is greatest at one end of the electrode and decreases along the length of the electrode. For example, in one embodiment the thickness of the coating is approximately 400 nanometers along a pre-set length of the electrode and then decreases in thickness, for example linearly or exponentially, until it reaches approximately zero near the opposite end of the electrode. The method generally comprises the rapid immersion of the metallic electrode into a bath along a predetermined orientation of immersion and up to a predetermined depth of immersion. The method further comprises a predetermined polarity of the electric charge, amplitude of the electric charge, and time of immersion. Finally, the method comprises the slow and controlled immersion of the metallic electrode from the bath along a pre-determined and variable speed course of extraction. Specifically, immersion of the electrode into the bath at a constant rate will produce a linear gradient in the thickness of the coating from the coated portion of the electrode to the end of the electrode. Furthermore, immersion of the electrode into the bath at a progressively increasing rate will produce an exponential gradient in the thickness of the coating from one end of the electrode to the other end of the electrode.

In another embodiment, the coated portion of the electrode comprises between 5% and 95% of the length of the electrode and the thickness of the coating is approximately zero at given portions of the length and varies according to a predetermined schedule at other portions of the length of the electrode. For example, in one embodiment a protective coating such as wax or photoresist is applied at portions of the length where it is desired to have approximately zero thickness of the coating, and the thickness of the coating varies from approximately 400 nanometers along a pre-set length of the electrode to approximately zero near the opposite end of the electrode. The method generally comprises the rapid immersion of the metallic electrode into a bath along a predetermined orientation of immersion and up to a predetermined depth of immersion. The method further comprises a predetermined polarity of the electric charge, amplitude of the electric charge, and time of immersion. Finally, the method comprises the slow and controlled immersion of the metallic electrode from the bath along a pre-determined and variable speed course of extraction. Specifically, immersion of the electrode into the bath at a constant rate will produce a linear gradient in the thickness of the coating from the coated portion of the electrode to the end of the electrode. Furthermore, immersion of the electrode into the bath at a progressively increasing rate will produce an exponential gradient in the thickness of the coating from one end of the electrode to the other end of the electrode.

Other features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF AN EMBODIMENT

Figure 2:
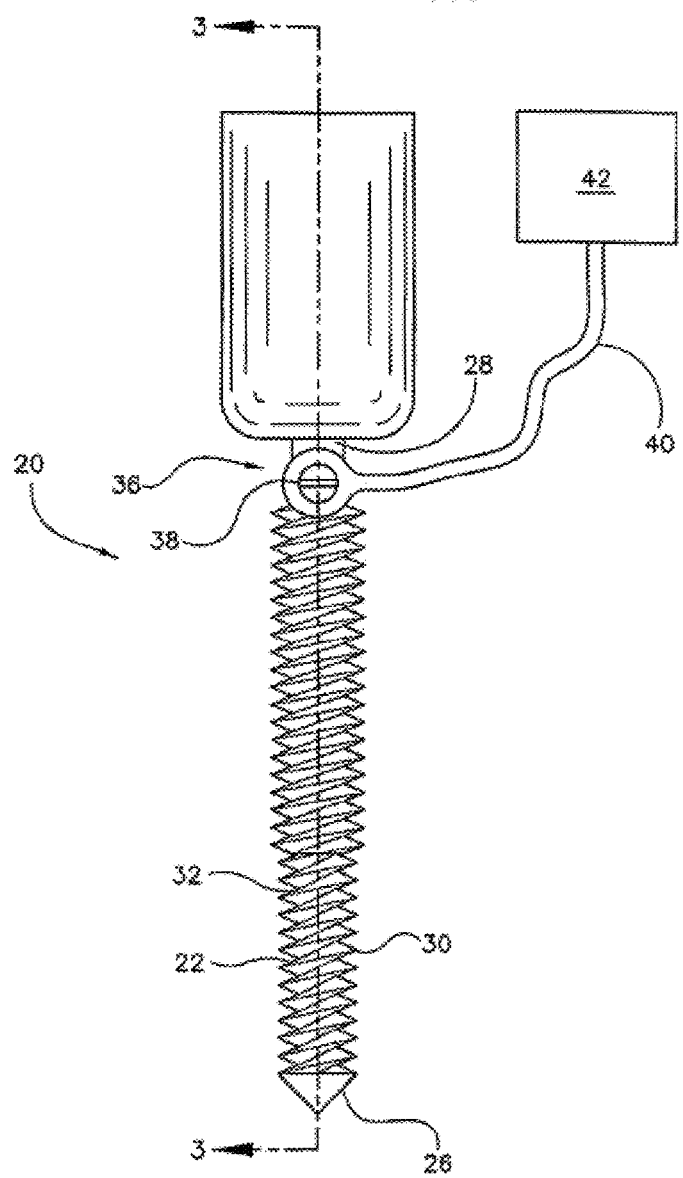
FIG. 2 is a side elevation of a screw of the present invention.

Referring now to the drawings and in particular to FIG. 2, a screw or electrode of the present invention is designated in its entirety by the reference numeral 20. The screw 20 has an elongate shaft 22 having a length 24 (FIG. 3) extending between opposite ends 26, 28. A conventional screw thread 30 is formed on an exterior surface 32 of the shaft 22. The thread 30 extends along at least a portion of the length 24 of the shaft 22. The screw 20 also includes a head 34 adjacent the one end 28 of the shaft 22. The head 34 is shaped for engaging the screw 20 with a driver or wrench to rotate the screw and thereby drive it into bone. In one embodiment, the screw 20 includes a connector, generally designated by 36, adjacent its head 34 for connecting an electrical conductor to the screw as will be explained in further detail below. In other embodiments, electrical current is coupled to the screw 20 through any other suitable coupling, such as through a rod or tulip. In general, the electrical connection is made to a portion of an assembly including the screw 20, where the assembly is fully insulated with the exception of the region where current is desired. In one embodiment, the connector 36 includes a screw fastener 38 threaded into the screw 20 for holding the electrical lead. As illustrated in FIG. 2, an electrical conductor 40 is electrically connectable to the screw 20 and to an electrical power source 42 for conveying electrical current through the shaft 22. In one embodiment the power source 42 produces direct current. In another embodiment, the power source 42 produces alternating current such as a time-varying current waveform (e.g., a sine wave or a square wave) having a frequency between nearly zero hertz and ten gigahertz. In yet another embodiment, the power source 42 provides a direct current to the screw 20 and/or provide a pulsed direct current to the screw via one or more waveforms such that periods of stimulation (i.e., periods of current being delivered to the screw) are intermixed with periods of recovery (i.e. periods where a reduced current or even no current is being delivered to the screw) as will be discussed more fully. Although other electrical conductors 40 may be used without departing from the scope of the present invention, in one embodiment the conductor is a 35 gauge insulated braided stainless steel wire. In other embodiments, the electrical conductor 40 may be omitted altogether, such as embodiments where the screw 20 receives an electrical current wirelessly or when the power source 42 is integral to the screw, as will be discussed more fully. It is further envisioned that the connector 36 may take other forms, for example but not limited to a rod or tulip. For example, the connector 36 may be a threaded terminal and nut, a fastenerless connector, a quick disconnect type connector, a soldered pin, or an adhesive without departing from the scope of the present invention. Further, and although in the depicted embodiment the conductor 40 is fixed generally perpendicular to an center axis of the screw 20 extending in a direction of the screw's length 24, in other embodiments the connector 36 may connect the conductor at any suitable angle relative to the center axis of the screw without departing from the scope of this disclosure. It will be apparent to those skilled in the arts that ground electrode may be separated into multiple components that are spatially separated.

According to an embodiment where screw 20 receives current wirelessly, a controller included in a first external circuit controls when power is transmitted to a second circuit formed by screw 20 and ground electrode. In this embodiment, said second circuit amounts to the secondary of an air-core transformer.

According to yet another embodiment, screw 20 comprises a screw body having a cavity, wherein power source 42 comprises a battery included in said cavity. A first terminal of power source 42 is attached directly to screw 20, while a second terminal of power source 42 is attached to a ground electrode.

Figure 3:
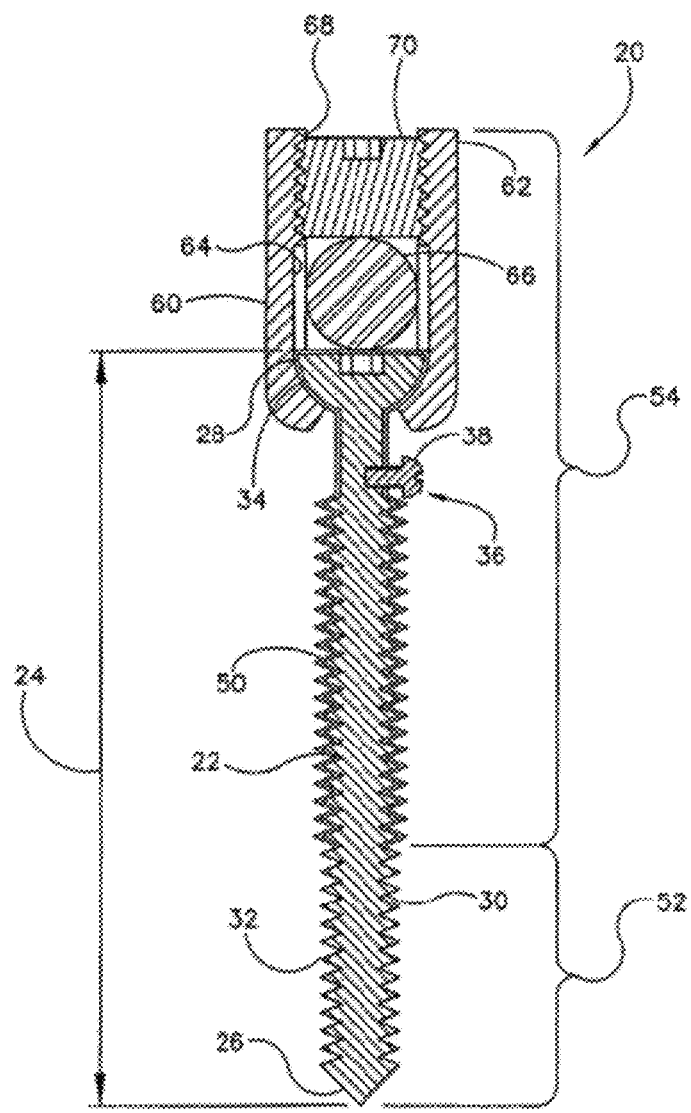
FIG. 3 is a cross section of the screw taken along line 3-3 of FIG. 2.

As illustrated in FIG. 3, the shaft 22 is generally conductive, but a portion of the shaft is coated with an insulating coating 50. Thus, the shaft 22 has an electrically conducting portion 52 and an electrically insulating portion 54. Although the conducting portion 52 of the screw 20 may have other lengths without departing from the scope of the present invention, in one embodiment the conducting portion of the screw has a length of less than about four centimeters. In one embodiment, the conducting portion 52 of the screw 20 has a length of between about three millimeters and about three centimeters. Further, although the conducting portion 52 of the screw 20 may be positioned at other locations along the screw, in one embodiment the conducting portion of the screw is positioned adjacent the end 26 of the screw opposite the head 34. In another embodiment (not shown), the conducting portion 52 of the screw 20 is positioned between the ends 26, 28 of the screw, and each end of the screw is electrically insulated. Although the insulating portion 54 of the screw 20 may have other lengths without departing from the scope of the present invention, in one embodiment the insulating portion of the shaft 22 extends at least forty percent of the length 24 of the screw. In another embodiment, the insulating portion 54 of the shaft 22 extends between about fifty percent of the length 24 of the screw 20 and about ninety five percent of the length of the screw.

In one embodiment, a clevis 60, sometimes referred to as a tulip, is attached to the screw 20. The clevis 60 pivots freely on the head 34 of the screw 20 and includes a pair of legs 62 defining an opening 64 adapted to receive a rod 66. The legs 62 include threads 68 for engaging a screw 20 for fastening the rod 66 in the opening 64 and preventing the clevis 60 from pivoting on the screw head 34. Other features of the screw 20 and clevis 60 are conventional and will not be described in further detail.

As will be appreciated by those skilled in the art, the screw 20 comprises an electrically conductive material such as a titanium alloy and the electrically insulating portion of the shaft is coated with an insulating material 50 such as titanium dioxide. In one embodiment, the insulating material 50 is formed by anodizing the exterior surface 32 of a portion of the shaft 22, including the head 34. In some embodiments, the insulating material 50 is an anodization layer with a variable thickness (i.e., a gradient), as will be discussed more fully. The conductivity of the screw 20 in the conducting portion 52 may be improved by coating the screw with a highly conductive material including but not limited to titanium nitride, platinum, or an alloy of platinum and iridium. Both treated surfaces, titanium dioxide and conductive material, are extremely adherent to the titanium and therefore not likely to be breached when screwed into bone. Because methods for anodizing and/or coating titanium parts are well known by those having ordinary skill in the art, they will not be described in further detail.

Figure 1:
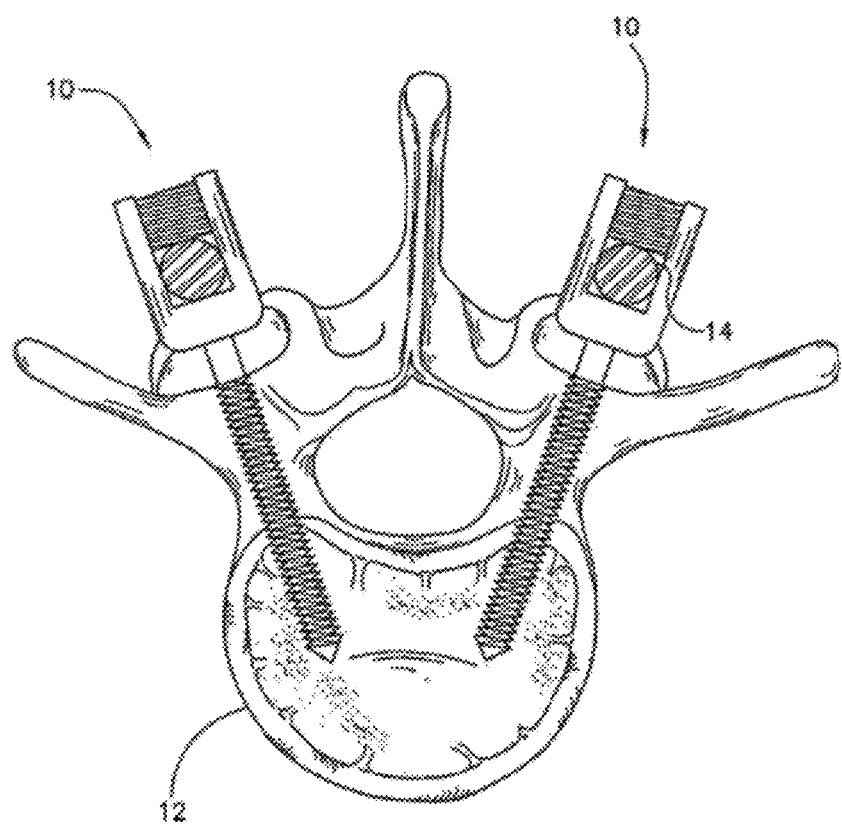
FIG. 1 is a horizontal cross section of a conventional electrically conductive screw installed in a vertebra.

The screw 20 is used in conjunction with a ground electrode (not shown) so that an electrical circuit is completed from electrical power source 42 into the bone or tissue into which the screw are driven, and thence to said ground electrode, which optionally may be a second screw. As will be appreciated by those skilled in the art, electrical current travels through the conductive portion 52 of the screw 20 from electrical power source 42 and/or conductor 40 to the bone in which the screw 20 is inserted (e.g., a vertebra such as vertebra 12 in FIG. 1) as will be explained in more detail below. The current does not pass through the coating 50 (e.g., anodization layer) on the insulated portion 54 of the shaft 22 so that the current may be directed to the portion of the bone or other tissue where stimulation is most needed. As will be also appreciated, the insulated portion 54 of the shaft 22 reduces current from passing through portions of the bone and tissue where electrical current is not desired. The screw 20 of the present invention may be installed in the bone using conventional techniques. In most instances, the bone is pre-drilled to avoid splitting when the screw 20 is installed. It is envisioned in some instances the bone may be reinforced, such as with bands before the screw 20 is installed to provide support to the bone and prevent damage to it as the screw is installed.

Figure 4:
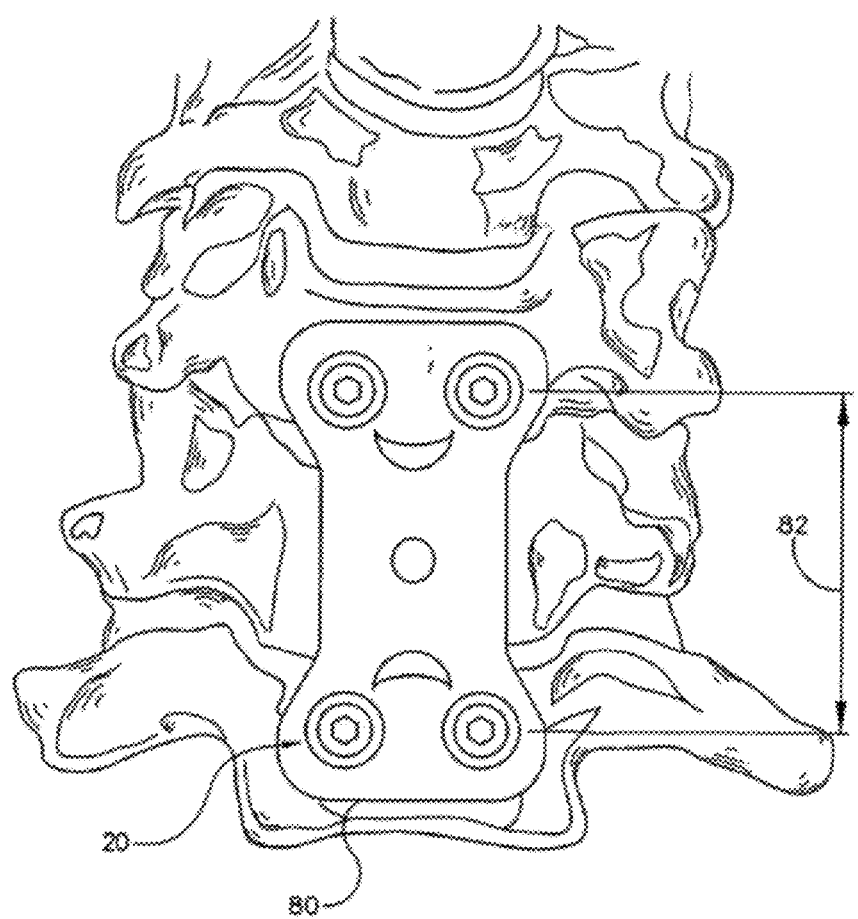
FIG. 4 is an front elevation of a portion of a spine with a first apparatus of the present invention including a plate installed thereon.
Figure 5:
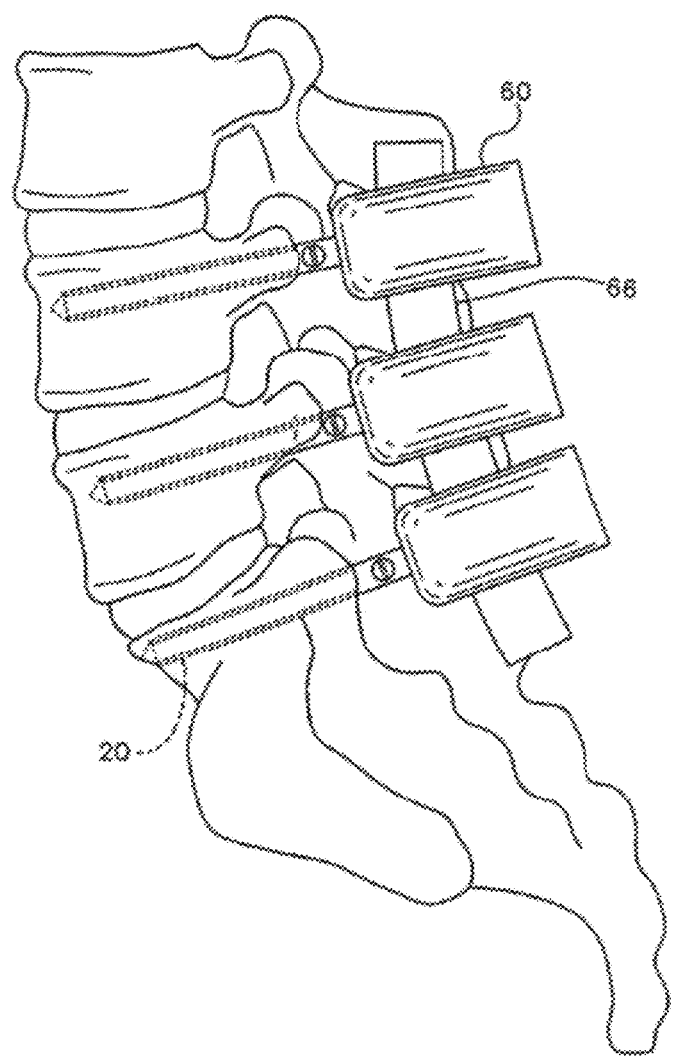
FIG. 5 is a side elevation of a portion of a spine with a second apparatus of the present invention installed thereon.

In some instances, it is envisioned that the screws 20 of the present invention may be used in combination with other appliances, such as spacers, BMP sponges, synthetic bone substitutes, IV discs, cages, etc. For example, in some applications the screws 20 may be installed through a plate 80 as shown in FIG. 4 to provide support for the bone and to guide proper spacing and positioning of the screws. In this embodiment, plate 80 has at least two openings (not shown) for receiving screws 20. Preferably, each of the openings are sized and shaped for receiving at least one screw 20. Although the openings in the plate 80 may have other spacing without departing from the scope of the present invention, in one embodiment the openings are spaced by a distance 82 of between about one centimeter and about two centimeters. In the embodiment shown in FIG. 5, the spacers are formed as rods 66 bridging the screws 20 as described above. Rods 66 and plate 80 are electrically conductive, but completely anodized. As the configurations shown in FIGS. 4 and 5 are otherwise known to those having ordinary skill in the art, they will not be described in further detail.

To use the apparatus of the present invention to stimulate bone growth, the bone (e.g., vertebra 12) is pre-drilled. A first screw 20 is inserted in the bone and driven into place by turning the screw. A second screw 20 is inserted in the bone at a predetermined distance from the first screw. In other embodiments, only first screw 20 is needed and second crew 20 is omitted. Next, an electrical connection is made, such as by attachment of conductors 40 to screws 20, rods 66, and/or clevis 60, between the screws 20 and to an electrical power source 42 (e.g., a generator, a battery or an inductance coil positioned in a pulsing magnetic field). The conductors 40 are energized by the power source 42 so an electrical current passes through the bone. As will be discussed in more detail, in some embodiments the conductor 40 may optionally be omitted, such as, e.g., in embodiments where the power source 42 is integral to one or more screws 20 and/or when one or more screws receive an electrical current wirelessly from the power source 42. Further, in some embodiments the conductor 40 may be attached to other components such as, e.g., the rods 66, which in turn may conduct the received current to the screws 20 as will be discussed more fully. Because the screws 20 are partially insulated, the electrical current passes between only a portion of the first screw and only a portion of the ground electrode directing the current to a particular area of the bone or tissue. Although other amounts of current may be used, in one embodiment a direct current of between about one microamp and about one milliamp is used. In another embodiment, a direct current of between about twenty microamps and about sixty microamps is used. In other embodiments, a direct current of about twenty, forty, sixty, eighty, or one hundred microamps is used. In other embodiments, the current may be any time-varying current waveform (e.g., a sine wave or a square wave) having a frequency between nearly zero hertz and ten gigahertz. In still other embodiments, a current may be pulsed, provided according to a duty cycle, and/or provided according to one or more waveforms such as a direct current sine wave or a direct current square wave as will be discussed more fully.

In addition to stimulating bone growth, it is envisioned that the apparatus and method described above may be used to improve tissue growth and healing, including soft tissue and nerve tissue. Thus, the apparatus and method may be useful in healing spinal cord and nerve root injury. Further, in some embodiments, the apparatus and method may be useful in treating pain syndromes.

Figure 6:
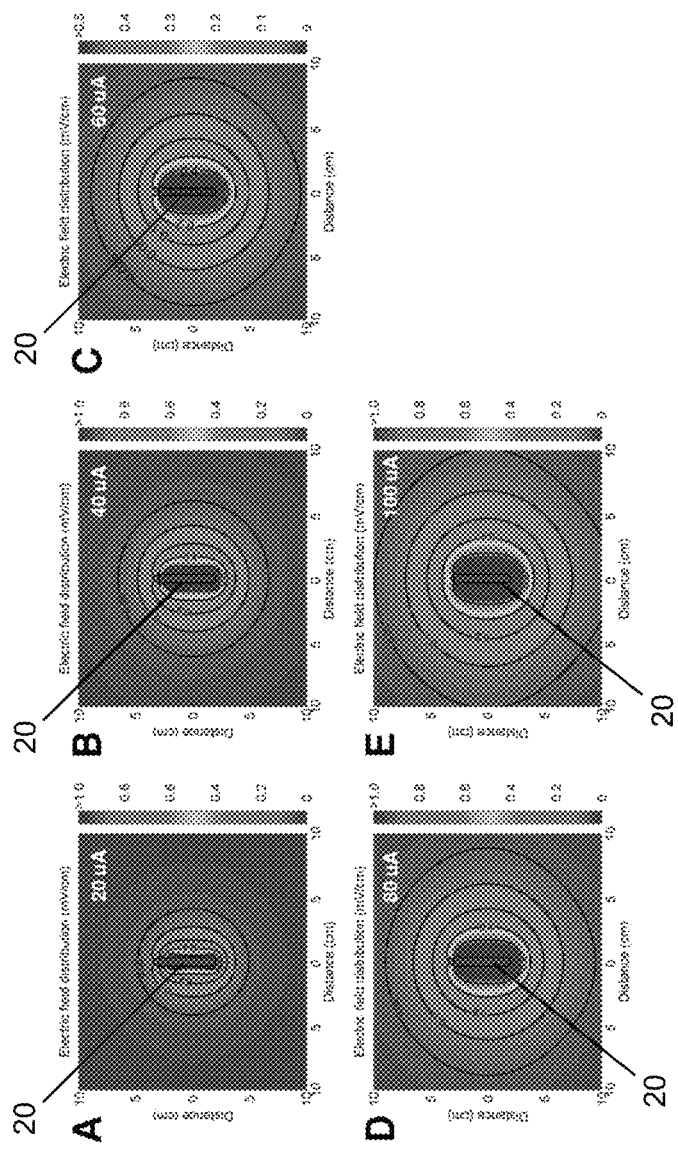
FIG. 6 is a schematic of electric fields induced by an unanodized screw for various levels of an applied direct current.

As discussed, in some embodiments the electrically conducting portion 52 of the screw 20 may extend for less than the entire length 24 of the screw. In such embodiments, an electric field induced in an environment where the screw 20 is implanted (e.g., a bone, tissue, etc.) may be altered and/or focused on an area of interest (i.e., an area of the bone/tissue requiring stimulation). This may be more readily understood with reference to FIG. 6. FIG. 6 illustrates an electric field induced by various amplitudes of an applied direct current for a screw 20 containing no insulating coating 50 (i.e., a screw with the electrically conducting portion 52 extending for the entire length 24 of the screw). More specifically, FIG. 6 illustrates an electric field induced by a screw 20 without the insulating coating 50 for a direct current stimulation of 20 microamps in FIG. 6A, 40 microamps in FIG. 6B, 60 microamps in FIG. 6C, 80 microamps in FIG. 6D, and 100 microamps in FIG. 6E. As depicted, when the screw 20 does not contain the insulating coating 50, the electric field induced in the bone and/or surrounding tissue where the screw is implanted is generally elliptical in shape and extends over the entire length 24 of the screw. Further, as the amplitude of the current applied to the screw 20 is increased, the amplitude of the induced electric field is generally increased as well. Thus, for a screw 20 containing no insulating coating 50, the electric field is not focused at any one portion along the length of the screw 20, but rather extends along the entire length of the screw. Further, if the amplitude of the induced electric field at any one point along the screw 20 needs to be increased (in order to, e.g., achieve appropriate osteogenic benefits) the amplitude along the entire length of the screw must be increased. This may result in electric fields being induced in areas not of interest (e.g., electric fields may be induced near the end 28 of the screw 20 where stimulation may not be needed). This may also result in large amounts of power consumed as the current applied to the screw may need to be dramatically increased in order to produce a desired amplitude of the induced electric field at the any of interest (i.e., the area of the bone and/or surrounding tissue requiring osteogenic stimulation).

Figure 11:
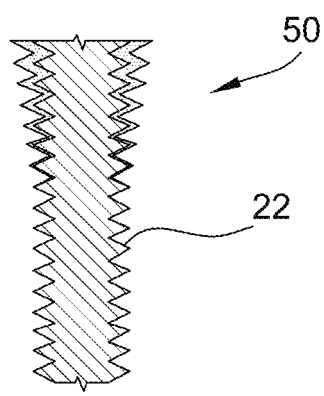
FIG. 11 is a cross section of a portion of a screw in which the thickness of an insulating coating is varied.

However, when the insulating coating 50 is applied to the screw 20 (such as by anodization or the like as discussed) forming the electrically insulating portion 54, the geometry of the induced electric field may be altered and the induced electric field may be more readily focused on the area of interest. In some embodiments, an anodization layer is applied to the screw over less than the entire length 24 of the screw forming the insulating coating 50. The thickness of the insulating coating 50 is directly related to the degree of insulation, current ejection, and resistance. In some embodiments, the insulating coating 50 has a substantially uniform thickness. In other embodiments, the thickness of insulating coating 50 is varied (as depicted in FIG. 11). This anodization layer (i.e., insulating coating) alters the geometry and intensity of the induced electric field at the area of interest. For example, a portion of the length 24 of the screw 20 may be uniformly anodized such that a thickness of the anodization layer is the same over the entire length of the insulating coating 50. In some embodiments, a relative length of the insulating coating 50 (i.e., the anodized region) of the screw 20 to the overall length 24 of the screw may be about 50%. In other embodiments, the length of the anodized region of the screw 20 relative to the overall length 24 of the screw may be about 75%, 90%, or even 95%.

Figure 7:
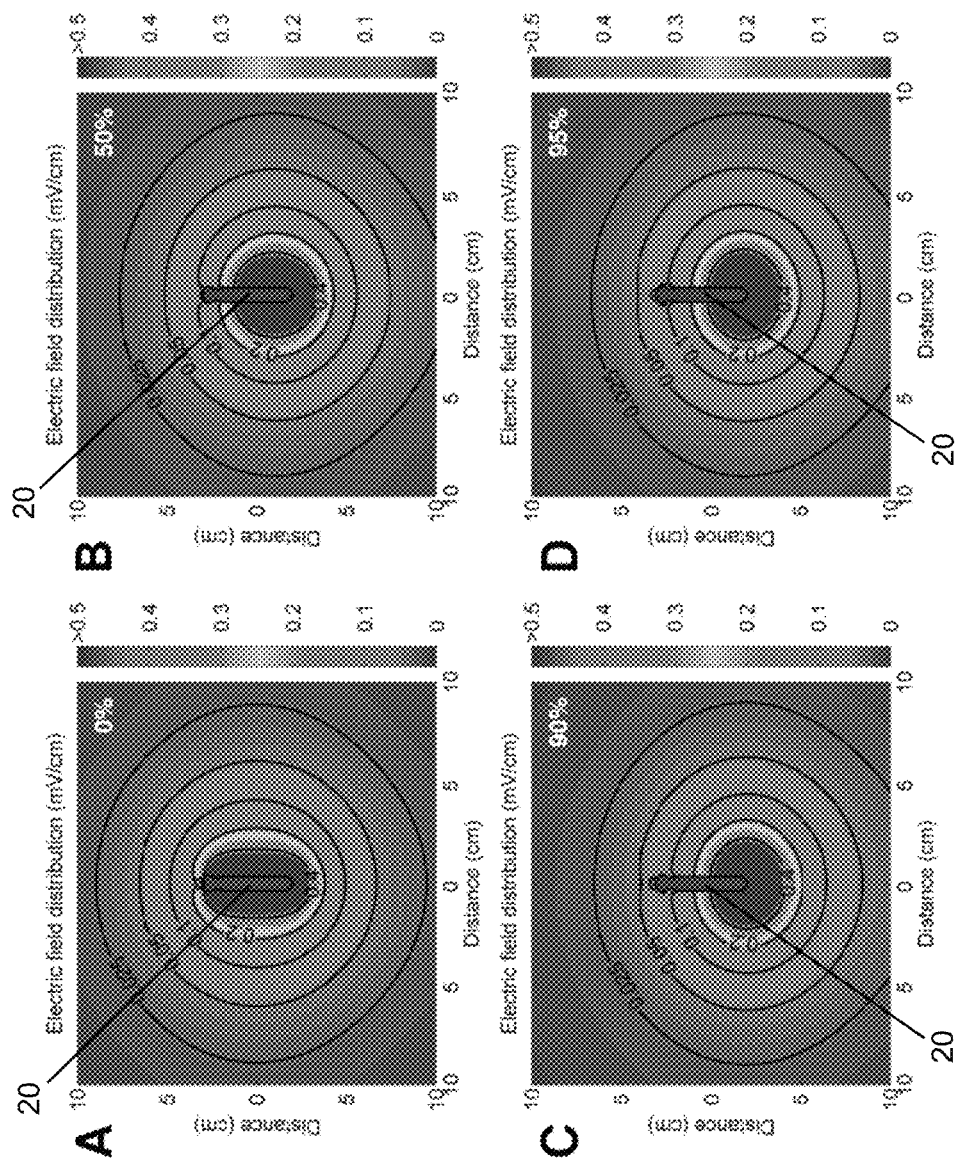
FIG. 7 is a schematic of an electric field induced by the unanodized screw and electric fields induced by three embodiments with anodization layers covering 50%, 90%, and 95% of the length of the screw.

In such embodiments, the geometry and amplitude of the induced electric field in the environment surrounding the screw 20 differs from the geometry and amplitude of the electric field induced by a screw containing no insulating coating 50 (as discussed in connection with FIG. 6). This may be more readily understood with reference to FIG. 7. FIG. 7 illustrates an electric field induced by a screw 20 comprising various lengths of the insulating coating 50 (i.e., the anodized region) for a constant supplied direct current. Specifically, FIG. 7A illustrates an electric field induced by a screw 20 having no portion of its length 24 anodized (similar to the screw discussed in connection with FIG. 6), FIG. 7B illustrates an electric field induced by a screw having 50% of its length anodized, FIG. 7C illustrates an electric field induced by a screw having 90% of its length anodized, and FIG. 7D illustrates an electric field induced by a screw having 95% of its length anodized. As discussed, for a screw 20 having no insulating coating 50, the induced electric field (as depicted in FIG. 7A) is approximately elliptical in shape and extends over the entire length 24 of the screw. However, for a screw 20 having an anodization layer (i.e., insulating coating 50), the induced electric field (as depicted in FIGS. 7B-7D for relative coating lengths of 50%, 90%, and 95%, respectively) is approximately spherical in shape. More particularly, when the screw 20 comprises the insulating coating 50, a spherical electric field is induced which is centered around the electrically conducting portion 52 of the screw.

Further, the amplitude of the induced electric field centered around the electrically conducting portion 52 of the screw 20 increases as the relative length of the insulating coating 50 increases for a constant direct current applied to the screw, which may increase the therapeutic effect. For example, for a given direct current (e.g., 40 microamps), the electric field induced near the end 26 of the screw 20 having 95% of its length anodized extends further into the bone and/or surrounding tissue and has a higher intensity than in embodiments where the screw has less than 95% of its length anodized. Moreover, the spatial distribution of the induced electric field extends farther from the surface of the screw. Accordingly, in some embodiments the length 24 of the screw 20 may be selectively anodized to control the induced electric field geometry and amplitude. Specifically, a portion of the length 24 of the screw 20 may be anodized in order to achieve a generally spherical electric field, and an appropriate percentage of the length of the screw may be anodized in order to concentrate the electric field on an area of interest (i.e., the volume of the bone and/or surrounding tissue requiring osteogenic stimulation). As a result, areas of interest within the bone and/or its surrounding tissue may be suitably stimulated while using less power and/or a decreased period of stimulation than is needed for screws 20 containing no insulating coating 50.

Figure 8:
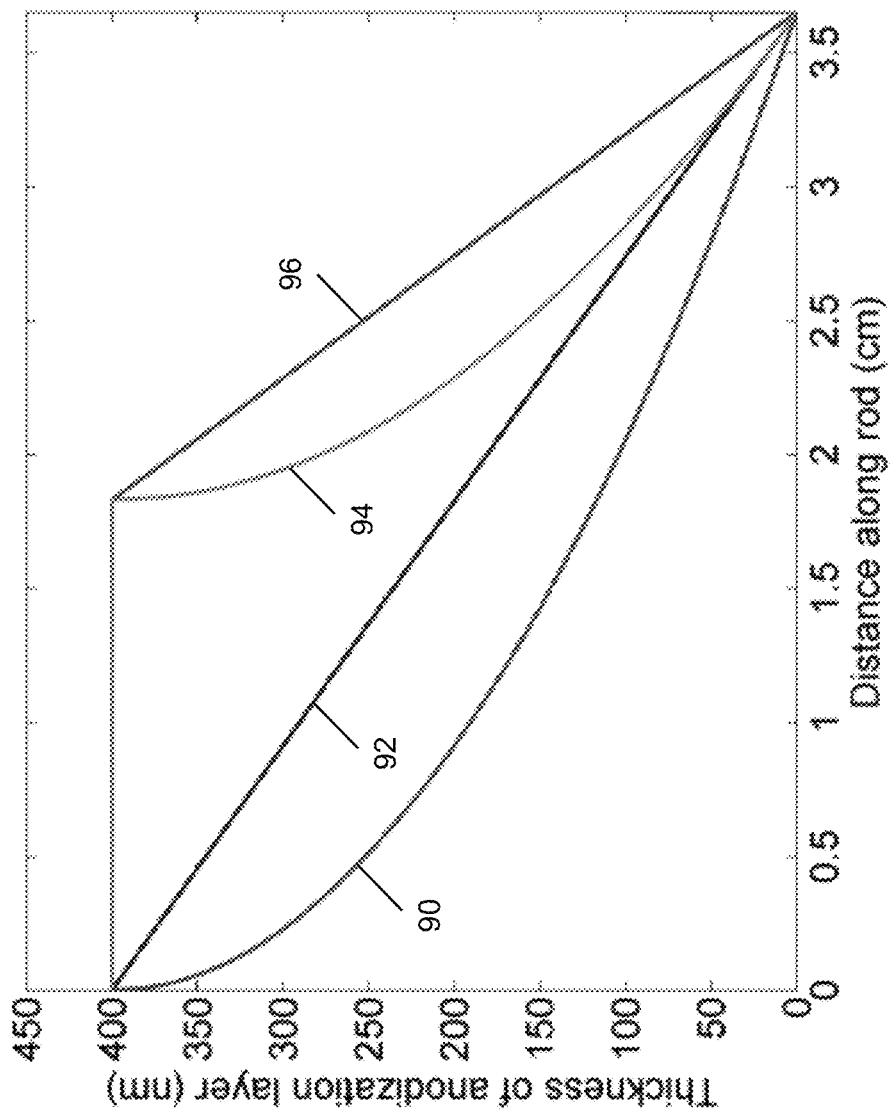
FIG. 8 is a plot depicting a thickness of an anodization layer on the screw for four different anodization gradients according to aspects of the disclosure.

In some embodiments, a thickness of the insulating coating 50 (e.g., a thickness of the anodization layer) may vary over the portion of the screw 20 containing the insulating coating, as depicted in FIG. 11, in order to produce a gradient of the insulating coating. For example, the thickness of the anodization layer may be greater at one point along the length 24 of the screw 20 than at another point, providing further osteogenic stimulation benefits. This may be more readily understood with reference to FIGS. 8 and 9. First, FIG. 8 depicts four plots illustrating a thickness of an anodization layer (i.e., insulating coating 50) over the length 24 of the screw 20 for four illustrative embodiments of the disclosure. More particularly, FIG. 8 depicts plots depicting the thickness of the anodization layer over the length 24 of the screw 20 for a 100% exponential gradient 90, a 100% linear gradient 92, a 50% exponential gradient 94, and a 50% linear gradient 96. Although FIG. 8 depicts specific thickness dimensions of the anodization layer for each embodiment (ranging from 400 nanometers to zero nanometers), it should be appreciated that in other embodiments the anodization layer may be any suitable thickness without departing from the scope of this disclosure. Further, while FIG. 8 only depicts gradients of the anodization layer covering either 100% of the length 24 of the screw 20 or 50% of the length of the screw, it should be appreciated that in other embodiments the gradient may cover any suitable percentage of the length of the screw without departing from the scope of this disclosure. In various embodiments, the percentage of the length of the screw 20 which is anodized can be any percentage and in any pattern (e.g., exponential, logarithmic, linear, etc.) suitable for a particular or general clinical application.

Returning to FIG. 8, in embodiments where the screw 20 comprises the 100% exponential gradient 90, the thickness of the anodization layer will be the greatest at one end of the screw 20 (i.e., either end 28 or end 26) and will decrease exponentially along the entire length of the screw 20. For example, in the depicted embodiment a thickness of the anodization layer is approximately 400 nanometers at the end 28 of the screw 20 and decreases in thickness exponentially until it reaches approximately zero near the opposite end 26 of the screw. Again, the specific dimensions depicted in FIG. 8 are merely illustrative and in other embodiments the thickness of the anodization layer along the length 24 of the screw 20 may vary from those depicted without departing from the scope of this disclosure. In embodiments where the screw 20 comprises the 100% linear gradient 92, the thickness of the anodization layer will be the greatest at one end of the screw 20 (i.e., either end 28 or end 26) and will decrease linearly (e.g., decrease at a constant rate) along the entire length 24 of the screw. For example, in depicted embodiment a thickness of the anodization layer is approximately 400 nanometers at the end 28 of the screw 20 and decreases in thickness linearly until it reaches approximately zero near the opposite end 26 of the screw. For the 50% exponential gradient 94 and the 50% linear gradient 96, the thickness of the anodization layer follows a similar pattern as that of the 100% exponential gradient 90 and the 100% linear gradient 92, respectively, except that each of the gradients 94, 96 maintain a constant thickness of the anodization layer over approximately 50% of the length 24 of the screw 20 (in the depicted embodiment, 400 nanometers), and then decreases in thickness along the rest of the length either exponentially (for the 50% exponential gradient) or linearly (for the 50% linear gradient).

Figure 9:
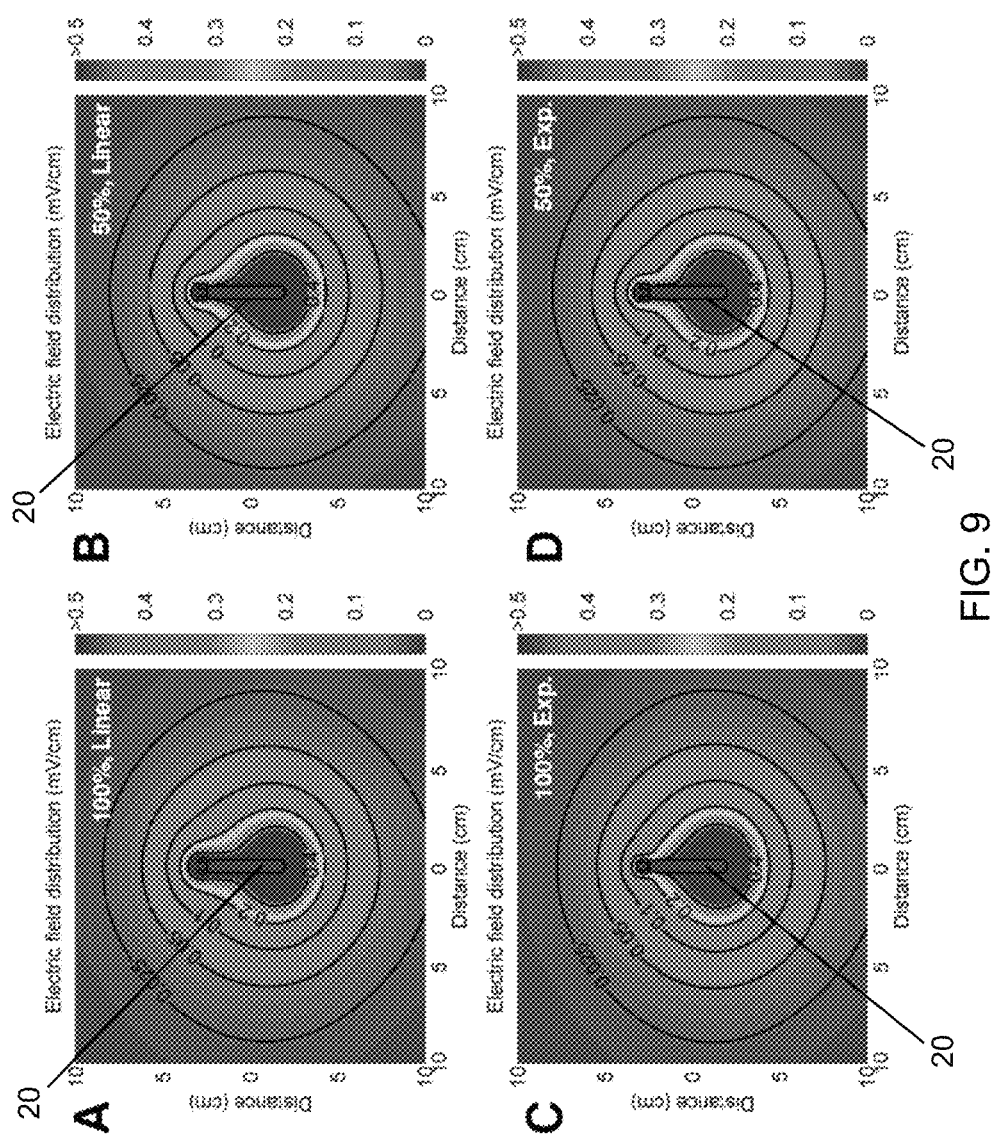
FIG. 9 is a schematic of an electric field induced by the screw employing each of the anodization gradients depicted in FIG. 8.

When the screw 20 comprises a graded anodization layer as described above, the geometry and amplitude of a resulting induced electric field may differ from those induced in embodiments where the screw comprises a uniform anodization layer thickness (as discussed in connection with FIG. 7) and in embodiments where the screw comprises no anodization layer (as discussed in connection with FIG. 6). This may be more readily understood with reference to FIG. 9. FIG. 9 depicts an induced electric field for the four anodization gradients depicted in FIG. 8 under a constant direct current. Specifically, FIG. 9A depicts an induced electric field for the 100% linear gradient 92, FIG. 9B depicts an induced electric field for the 50% linear gradient 96, FIG. 9C depicts an induced electric field for the 100% exponential gradient 90, and FIG. 9D depicts an induced electric field for the 50% exponential gradient 94. As seen, when the screw 20 comprises an insulating coating 50 with a varying thickness (e.g., a graded anodization layer as depicted in FIG. 11) the resulting induced electric field is generally pear-shaped (i.e., it includes a relatively narrow elongated portion along a portion of the shaft of the screw 20 that relatively rapidly expands to broader, rounder shape). More particularly, the induced electric field near a distal end 26 of the screw 20 is higher in amplitude and extends over a larger spatial region, while the induced electric field near the proximal end 28 of the screw is lower in amplitude and extends only a small distance from the screw exterior surface 32. Further, for gradients where the thickness of the anodization layer over half of the length 24 of the screw 20 was kept constant (e.g., the 50% exponential gradient 94 and the 50% linear gradient 96), the amplitude of the induced electric field is also pear shaped yet the electric field near the distal end 26 is even higher in intensity and extends further from the exterior surface 32 of screw, and the electric field near the proximal end 28 is even lower in amplitude and extends a smaller distance from the exterior surface of the screw.

Thus, in some embodiments the screw 20 may be selectively anodized with a graded anodization layer in order to control the induced electric field geometry and amplitude. Specifically, a portion of the length 24 of the screw 20 may be anodized with at least part of the anodized portion having a varying thickness of the anodization layer in order to achieve a generally pear-shaped electric field. As a result, areas of interest within the bone and/or its surrounding tissue may be suitably stimulated while using less power and/or a decreased period of stimulation than is needed for screws 20 containing no insulating coating 50.

In some embodiments, the screw 20 may be selectively anodized in order to achieve desired properties for a particular clinical setting. That is, depending on the specific bone, tissue, etc., ultimately stimulated by the screw 20, one or more of the above discussed anodization layer patterns may be applied such that an electric field induced by the screw delivers an appropriate electric field to a stimulated area of interest.

For example, and as will be appreciated by those having skill in the art given the benefit of this disclosure, in some embodiments the screw 20 may be implanted in or near human vertebrae (as depicted in FIGS. 4 and 5) to provide osteogenic stimulation to the vertebrae and/or the surrounding tissue. In such embodiments, the anodization pattern of the screw 20 may be configured according to a specific region requiring stimulation. For example, in embodiments where stimulation is desired in the intervertebral (IV) space or a vertebral body, an uniform anodization pattern with 95% or more of the length 24 of the screw 20 anodized may provide the greatest osteogenic benefits. However, in embodiments where stimulation is desired in an instrumented pedicle, an exponentially or linearly graded anodization pattern (as compared to a uniform anodization pattern) may provide the greatest osteogenic benefits. Further, in embodiments where stimulation is desired in each of the IV space, the vertebral body, and the instrumented pedicle, a linearly graded anodization layer (such as a 100% linearly graded anodization layer) may provide the greatest osteogenic benefits. Accordingly, a length of the anodization layer on the screw 20 and/or a gradient of the anodization layer on the screw may be configured according to a desired osteogenic application of the screw.

In some embodiments, selective anodization (using any of the anodization patterns as discussed) may be provided anywhere along the length 24 of the screw 20, as depicted in FIG. 11, without departing from the scope of this disclosure. For example, in some embodiments the screw 20 may comprise the conducting portion 52 of the screw at a different relative location than that depicted in, e.g., FIG. 3. More particularly, in some embodiments the conducting portion 52 of the screw 20 may be positioned between the ends 26, 28 of the screw, with each end of the screw being electrically insulated. In such embodiments, an anodization layer may be provided to each of the ends 26, 28 of the screw forming the insulating coating 50, with a portion of the screw between the anodization layers left exposed to form the conducting portion 52. The anodization layers provided to either end may employ any of the above discussed anodization patterns. For example, in some embodiments, a thickness of the anodization layers at the ends 26, 28 of the screw 20 may be greater than a thickness of the anodization layer nearer a midpoint of the screw 20 such that that one or more of the above discussed benefits of the graded anodization layer is provided at a different relative location along the screw. Generally, the length and position of the unanodized/uncoated region of the screw 20 may be varied depending on the configuration and the specific clinical application.

In some embodiments, the electrical conductor 40 may be omitted without departing from the scope of the disclosure. For example, in some embodiments, the electrical power source 42 may be integral to the screw 20, such as in the form of a battery. In other embodiments, the electrical power source 42 may be external to the screw 20 but may nonetheless not be connected to the screw. For example, the electrical power source 42 may conduct electricity to the screw 20 via one or more well-known wireless power delivery methods.

Further, and because an intensity and/or relative spatial distance of the induced electric field of the screw 20 may be increased for a given applied DC current as compared to known electric stimulators as discussed, less current may ultimately be needed to achieve a desired electric field intensity and associated osteogenic stimulation. For example, in embodiments where the screw 20 is anodized over 95% of its length, induced electric fields within the IV space and vertebral body may be over 500% greater in amplitude than those induced by unanodized screws (i.e., screws containing no insulating coating 50). Accordingly, this may lead to increased battery life and/or reduced power consumption as compared to known electric stimulators. In such embodiments, an internal battery and/or wireless power delivery may be used even if such delivery methods were previously impractical due to the relatively high current needed for unanodized screws 20 as discussed.

In other embodiments, the electrical conductor 40 may be connected to one or more of the rods 66 rather than to the screw 20. In such embodiments, a current supplied by the electrical power source 42 will be supplied to the rods 66 which in turn will conduct the current to one or more screws 20 integrally attached via the rods 66 (as discussed). In such embodiments, an electric current may be distributed evenly over each screw 20 thus providing for uniform stimulation and/or power consumption by each screw.

According to some aspects, a current supplied to the screw 20 by the power source 42 may be pulsed and/or may be provided intermittently. For example, in some embodiments the power source 42 may pulse direct current to the screw 20 (either directly or via the rod 66, etc., as discussed) following a predetermined time interval schedule. In other embodiments, the power source 42 may provide direct current to the screw 20 following a predetermined duty cycle. For example, for a 10% duty cycle, the power source 42 may supply electric current to the screw 20 10% of the time while not supplying an electric current for 90% of the time. In still other embodiments, the power source 42 may supply direct current to the screw 20 following a predetermined waveform or the like. For example, in some embodiments the power source 42 may supply a direct current to the screw by varying the amplitude of current being supplied according to, e.g., a square wave, sine wave, etc. In any event, supplying a current to the screw 20 intermittently may provide benefits over known power delivery systems, such as reduced electrochemical reactions at the screw 20 surface, and improved tissue healing and bone formation. For example, applying a current to the screw 20 may stimulate an area of interest and thus provide the osteogenic benefits as discussed. However, intermittent periods of a reduced current or no current being supplied may allow for periods of recovery and thus may further promote bone growth, etc. Further, and particularly when combined with a selectively applied anodization layer as discussed, embodiments of the invention may lead to reduced power consumption and/or increased battery life. Reduced power consumption and/or increased battery life may improve device longevity and reduce the need for surgical replacement of the battery, thereby reducing clinical risk and complications for patients.

In some embodiments, a duty cycle/pulsed schedule, etc., applied to the screw 20 may be varied according to a present phase of recovery for the bone and/or its surrounding tissue. For example, in some applications it may be more beneficial to apply increased stimulation (e.g., electric current) to an area of interest early in a recovery process. Thus, for a period of time directly following implanting the screw 20, a direct current may continuously or nearly continuously be provided to the screw 20. However, as time passes and the area of interest begins to heal (e.g., new bone forms, etc.) the periods of stimulation may be reduced. For example, the duty cycle of an applied direct current may be gradually reduced over time allowing for intermittent periods of recovery until the bone/tissue, etc., is fully healed. In one example, a direct current may be supplied to the screw 20 following a 100% duty cycle shortly after implanting the screw in the bone, such that the area of interest is always stimulated early in the healing process. However, as the bone and/or its surrounding tissue begins to heal, the duty cycle may be reduced such that the area of interest is provided both periods of stimulation (i.e., periods when the current is supplied to the screw 20) and periods of recovery (i.e., periods when the current is not supplied to the screw). Accordingly, in some embodiments a combination of a selectively applied anodization layer combined with an appropriate duty cycle may provide increased osteogenic benefits over known stimulation techniques.

Figure 10:
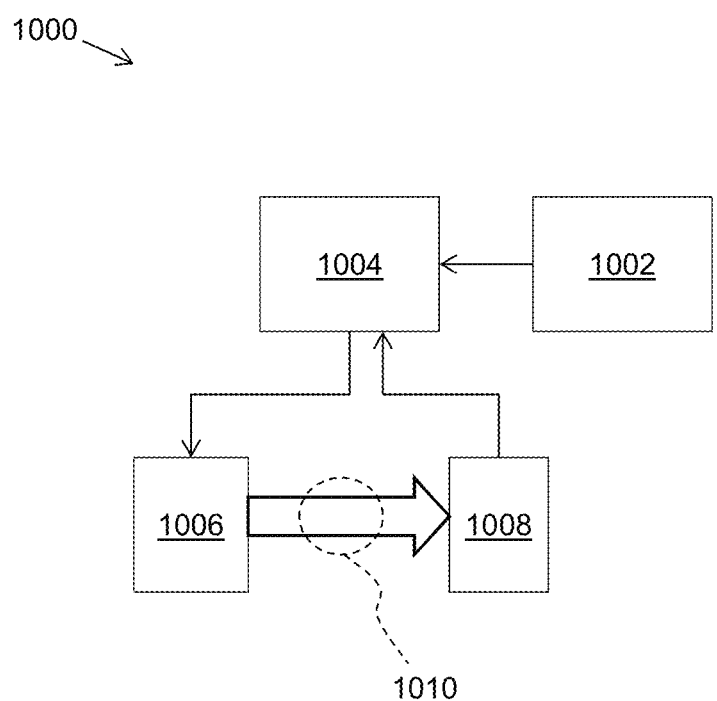
FIG. 10 is a schematic of a system comprised of a battery, a controller for adjusting application of D.C. current over time, a screw functioning as a first electrode, and a ground electrode.

FIG. 10 is a simplified block diagram of a system 1000 according to the present disclosure. The system 1000 includes a power source 1002, a controller 1004, a first electrode 1006, and a second electrode 1008. The system 1000 may be used for any suitable application described herein. In some embodiments, the system 1000 is used for one or more of stimulating bone growth, tissue healing, and pain control. The power source 1002 provides power to the system 1000. In an example embodiment, the power source is a DC power source, such as one or more batteries, capacitors, photovoltaic modules, power converters (AC/DC or DC/DC), etc. In some embodiments, the power source 1002 includes the power source 42.

The power source 1002 is coupled to controller 1004. The controller 1004 controls and adjusts the application of DC current over time as described herein. The controller 1004 may be any combination of digital and/or analog circuitry suitable for controlling the application of DC current as described herein. In some embodiments, the controller 1004 includes a processor and a memory (not shown). The processor executes instructions that may be stored in the memory. The processor may be a set of one or more processors or may include multiple processor cores, depending on the particular implementation. Further, the processor may be implemented using one or more heterogeneous processor systems in which a main processor is present with secondary processors on a single chip. In another implementation, the processor may be a homogeneous processor system containing multiple processors of the same type. The memory is any tangible piece of hardware that is capable of storing information either on a temporary basis and/or a permanent basis. The memory may be, for example, without limitation, random access memory (RAM) such as dynamic RAM (DRAM) or static RAM (SRAM), read-only memory (ROM), erasable programmable read-only memory (EPROM), electrically erasable programmable read-only memory (EEPROM), non-volatile RAM (NVRAM), and/or any other suitable volatile or non-volatile storage device.

The controller is coupled to the first electrode 1006 and the second electrode 1008 to selectively direct current from the power source 1002 to an area of interest 1010. The area of interest 1010 may be an area or a volume of a patient in which treatment using system 100 is desired. In the exemplary embodiment, the first electrode is a screw, such as the screw 20. Although a single first electrode 1006 is illustrated, the system 1000 may include any number of first electrodes 1006, each of which may selectively receive current from the controller 1004. The second electrode 1008 is a ground electrode. The system 1000 may include one or a plurality of ground electrodes 1008. The controller 1004 controls application of current from the power source 1002 to the first electrode 1006. The current passes from the first electrode 1006, through the area of interest 1010, and to the second electrode 1008. In the illustrated embodiment, the second electrode is coupled to the controller 1004. In other embodiments, the second electrode is coupled to the power source 1002.

Although the components of the system 1000 are illustrated as separate components, they may be separate components or may be integrated together. For example, in some embodiments, the controller is integrated with the first electrode 1006. In some embodiments, the power source 1002 is integrated with one or more of the controller 1004, the first electrode, and the second electrode. Moreover, the components of the system 1000 may be coupled together by any suitable wired or wireless connection. For example, the power source may inductively couple power to the controller 1004 for distribution through the electrodes 1006 and 1008.

The systems and methods described herein, including system 1000, may be used for many different clinical applications. For example, the systems and methods described herein can be utilized in spinal surgery for the purposes of accelerating bony fusion. They may be used in the design of pedicle screws, lateral mass screws, cortical screws used in and around the spine. They may also be used in the creation of custom spinal systems and instrumentation including rods, plates, screw caps, tulips, clips, etc. The methods and systems may also be applied to screws and/or implantable device(s) used in the creation and implementation of inter-body spacers, artificial discs, and the like.

The systems and methods described herein can be utilized in the design of instrumentation for use in the case of a bony fracture, which requires internal fixation and the use of screws, instrumentation, and/or metallic hardware. They may be used in the design of cortical screws used to stabilize and fix bony fractures of any bone. More specifically, the systems and methods may be used in the design of cortical screws used to stabilize and fix bony fractures of long bones with a high rate of non-union. The systems and methods may be used in the design of pins, wires, rods, and/or plates used to fix and stabilize broken, damaged, or diseased bone or bone tissues.

The systems and methods described herein can be applied to the design of metallic implants commonly used in joint reconstruction. For example, they may be used in the design of artificial metallic hip implants include hip stems, femoral stems, femoral implants, acetabular implants, cups, and associated screws or metallic fixtures or instrumentation. The methods and systems may also be used in the design of artificial metallic knee joints, elbow joints, shoulder joints, etc. including balls, stems, cups, and associated metallic fixtures and instrumentation.

The systems and methods described herein may be utilized in dental implant systems including endodontic, orthodontic, and oral surgery applications. Specifically, they may be utilized in dental implant systems such as dental posts, mandibular implants, screws, abutments, bridges, crowns, etc.

The systems and methods described herein may be utilized in instrumentation and fixation devices for reconstructive surgery. For example, the systems and methods may be utilized in fixation systems used to secure, mend, and fix broken bones in the face, hand, skull, etc. Moreover, they may be used to design screws, plates, and/or fixation systems for use in closing and fixating the skull following neurosurgery, trauma, cranial closure, etc.

The example methods and systems may be used with metallic implants and screws designed to resorb bone in areas of undue bone formation as a result of pathologies or disease. For example, they may be utilized in pins or screws utilized to resorb bone and/or osteophytes surrounding joints affected by osteoarthritis, rheumatoid arthritis, etc. They may be used in the treatment of medical conditions involving global overactive or improper bone growth such as fibrodysplasia ossificans progressive (FOP), diffuse idiopathic skeletal hyperostosis (DISH), ankylosing spondylitis, heterotopic ossification. Some embodiments may be used for removal of bone masses in medical conditions involving neoplastic bone formation or bony tumors such as osteosarcoma, chondrosarcoma, Ewing's sarcoma, osteoblastoma, osteoid osteoma, etc. Similarly, the methods and systems described herein may be used in the removal of osteophytes (i.e. "bone spurs") formed in the foot, shoulder, neck, spine, etc. as a result of chronic osteoarthritis, rheumatoid arthritis, reactive arthritis, rotator cuff injuries, plantar faciitis, spondylosis, and/or spinal stenosis.

Although various embodiments were described herein with reference to human applications, the methods and systems described herein may also be used in similar manners and for similar purposes in non-human applications, such as veterinary applications, including canine and equine applications.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A screw for use in stimulating at least one of bone growth, tissue healing, and pain control comprising:
an elongate shaft having a length extending between opposite ends, an exterior surface, and a screw thread formed on the exterior surface of the shaft and extending along at least a portion of the length of the shaft, said exterior surface of the shaft including at least a portion of the screw thread having an insulating coating extending along at least a portion of the length of the shaft;
a head adjacent one end of the shaft for engaging the screw to rotate the screw and thereby drive it into bone; and
an electrical conductor electrically connectable to the shaft for conveying current through the shaft,
wherein a thickness of the insulating coating at a first portion of the shaft is greater than a thickness of the insulating coating at a second portion of the shaft.

2. The screw set forth in claim 1, wherein the insulating coating is disposed adjacent to both the opposite ends of the shaft, and wherein the insulating coating does not cover a middle portion of the shaft disposed between the two opposite ends.

3. The screw set forth in claim 2, wherein the first portion is disposed at a first of the opposite ends of the shaft, wherein the second portion is disposed adjacent the middle portion of the shaft, and wherein the insulating coating decreases in thickness along the length of the shaft from the first portion to the second portion.

4. The screw set forth in claim 1, wherein the insulating coating extends between forty percent of the length of the shaft and ninety five percent of the length of the shaft.

5. An apparatus for stimulating at least one of bone growth, tissue healing, and pain control comprising:
an electrical power source; and
a plurality of electrodes electrically connected to the electrical power source, at least one of said electrodes has a tip and threads adapted for screwing into a patient and an insulating coating extending along at least a portion of a length of the exterior surface of at least one electrode and covering at least a portion of the threads,
wherein a thickness of the insulating coating at a first portion of the at least one electrode is greater than a thickness of the insulating coating at a second portion of the at least one electrode.

6. The apparatus set forth in claim 5, wherein the insulating coating extends between forty percent of the length of the at least one electrode and ninety five percent of the length of the at least one electrode.

* * * * *